(12) United States Patent
Roy et al.

(10) Patent No.: US 9,101,541 B2
(45) Date of Patent: Aug. 11, 2015

(54) STABLE SOLID PHARMACEUTICAL MATRIX COMPOSITIONS OF SIROLIMUS

(75) Inventors: Sunilendu Bhushan Roy, Gujarat (IN); Sushrut Krishnaji Kulkarni, Gujarat (IN); Kiritkumar Maulik Panchal, Gujarat (IN); Shubhashchandra Shailendra Mandge, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 69 days.

(21) Appl. No.: 13/643,386

(22) PCT Filed: Apr. 25, 2011

(86) PCT No.: PCT/IN2011/000269
§ 371 (c)(1),
(2), (4) Date: Dec. 19, 2012

(87) PCT Pub. No.: WO2011/135580
PCT Pub. Date: Nov. 3, 2011

(65) Prior Publication Data
US 2013/0095144 A1    Apr. 18, 2013

(30) Foreign Application Priority Data
Apr. 28, 2010   (IN) .......................... 1355/MUM/2010

(51) Int. Cl.
A61K 9/14    (2006.01)
A61K 9/16    (2006.01)
A61K 9/28    (2006.01)
A61K 31/436  (2006.01)
A61K 9/20    (2006.01)

(52) U.S. Cl.
CPC ............... *A61K 9/145* (2013.01); *A61K 9/1623* (2013.01); *A61K 9/1652* (2013.01); *A61K 9/2866* (2013.01); *A61K 31/436* (2013.01); *A61K 9/1694* (2013.01); *A61K 9/2018* (2013.01)

(58) Field of Classification Search
CPC .......................... A61K 9/1652; A61K 9/1694
See application file for complete search history.

(56) References Cited

U.S. PATENT DOCUMENTS

| | | | | |
|---|---|---|---|---|
| 5,989,591 | A | * | 11/1999 | Nagi .............................. 424/493 |
| 2003/0054042 | A1 | | 3/2003 | Liversidge |
| 2006/0094744 | A1 | | 5/2006 | Maryanoff |
| 2009/0068266 | A1 | | 3/2009 | Raheja et al. |

FOREIGN PATENT DOCUMENTS

| | | |
|---|---|---|
| EP | 1 938 800 A1 | 7/2008 |
| WO | 2007/027819 A2 | 3/2007 |

OTHER PUBLICATIONS

Marty, Francisco M., et al., "Voriconazole and Sirolimus Coadministration after Allogeneic Hematopoietic Stem Cell Transplantation", Biology of Blood and Marrow Transplantation 12:552-559(2006).

* cited by examiner

*Primary Examiner* — Carlos Azpuru
(74) *Attorney, Agent, or Firm* — Ladas & Parry LLP

(57) ABSTRACT

The present invention discloses a stable solid pharmaceutical matrix composition comprising sirolimus or pharmaceutically acceptable salts thereof along with one or more sugars.

15 Claims, No Drawings

STABLE SOLID PHARMACEUTICAL MATRIX COMPOSITIONS OF SIROLIMUS

RELATED APPLICATION INFORMATION

This application is a 371 of International Application PCT/IN2011/000269 filed 25 Apr. 2011 entitled "Pharmaceutical Compositions Of Sirolimus" which was published in the English language on 3 Nov. 2011, with International Publication Number WO 2011/135580 A2, and which claims priority from Indian Patent Application No.: 1355/MUM/2010 filed 28 Apr. 2010, the contents of which are incorporated herein by reference.

FIELD OF THE INVENTION

The present invention relates to pharmaceutical compositions of sirolimus or pharmaceutically acceptable salts thereof for oral administration. The compositions of the invention comprise sirolimus or pharmaceutically acceptable salts along with one or more sugars in a matrix based system. These compositions exhibit excellent stability. The invention also includes processes for the preparation of such compositions.

BACKGROUND OF THE INVENTION

Sirolimus, also known as rapamycin, an immunosuppressant drug used to prevent rejection in organ transplantation. It is especially useful in kidney transplants.

Sirolimus is a macrocyclic lactone produced by *Streptomyces hygroscopicus*. Chemically, it is (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29 (4H,6H,31H)-pentone, having a structure of Formula I.

[Formula I]

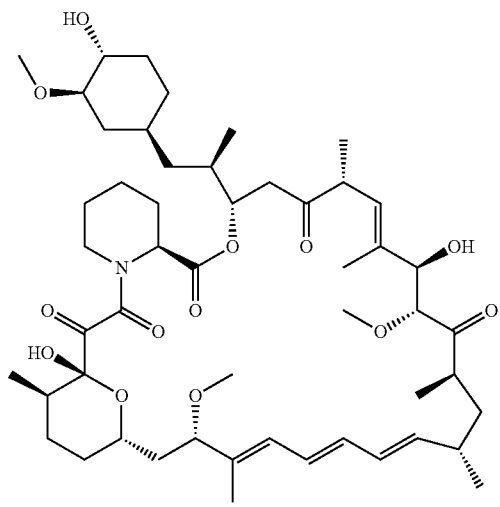

U.S. Pat. Nos. 5,100,899, 5,212,155, 5,308,847 and 5,403,833 disclose methods of inhibiting transplant rejection in mammals using sirolimus and derivatives and prodrugs thereof.

U.S. Pat. No. 5,145,684 discloses dispersible particles consisting essentially of a crystalline drug substance having a surface modifier adsorbed on the surface thereof in an amount sufficient to maintain an effective average particle size of less than about 400 nm and methods for the preparation of such particles and dispersions containing these particles.

U.S. Pat. Nos. 5,516,770 and 5,530,006 disclose intravenous sirolimus formulations.

U.S. Pat. Nos. 5,536,729 and 5,559,121 disclose liquid oral sirolimus formulations.

U.S. Pat. Nos. 5,989,591 and 5,985,325 disclose a solid dosage unit of sirolimus comprising a core and a sugar overcoat, said sugar overcoat comprising sirolimus, one or more surface modifying agents, one or more sugars, and optionally one or more binders.

Sirolimus is marketed by Wyeth under the trade name Rapamune® as 0.5 mg, 1 mg and 2 mg oral tablets for the prophylaxis of organ rejection in patients aged 13 years or older receiving renal transplants. It is also available as an oral solution containing 1 mg/ml sirolimus.

Sirolimus is described as BCS Class 2 drug in Pharmaceutical Research, Vo. 22, No. 1, January 2005 by Chi-Yuan Wu et al. Because of its poor water and oil solubility, only few formulations of rapamycin have proven satisfactory. Rapamycin is stable but not bioavailable if it is a crystalline solid with large particle size. Further, rapamycin is bioavailable but not stable as a micronized material. Hence, the challenge was to design a bioavailable and stable solid oral dosage form of rapamycin. The solution to this as known in the art as of today is nanonization of rapamycin by means of nanotechnology and to stabilize the nanosized particles and thereby develop a stable and bioavailable solid oral dosage form.

Nanonization of poorly soluble drug is a complex process and requires additional step during manufacturing. Nanonization increases the surface area available for dissolution; however, it also increases the change in free energy of the system when exposed to an aqueous solution. This results in particle aggregation and decreases the dissolution rate. Also, very fine nanosized particles are difficult to handle due to static charge that develops on particle surface during processing.

Moreover, sirolimus is known to have poor oil and water solubility. It is rapidly but poorly absorbed following oral administration with an approximate oral bioavailability of 15%. It reaches maximum blood concentrations in 0.5-2.3 hours after dosing. However oral formulations of rapamycin have restrictions due to their low solubility.

There is therefore an existing and continual need for stable and therapeutically equivalent oral solid pharmaceutical compositions of sirolimus. The compositions of the invention overcome all the encountered problems exemplified above.

SUMMARY OF THE INVENTION

In one general aspect, there is provided a stable solid pharmaceutical matrix composition comprising sirolimus or pharmaceutically acceptable salts thereof along with one or more sugars.

In another general aspect, there is provided a stable solid pharmaceutical matrix composition comprising sirolimus or pharmaceutically acceptable salts thereof along with one or more sugars in said matrix, wherein the sirolimus or pharmaceutically acceptable salt thereof have a $D_{90}$ particle size less than about 10 μm.

Embodiments of the pharmaceutical composition may include one or more of the following features. For example, the pharmaceutical composition may further include one or more pharmaceutically acceptable excipients. The pharmaceutically acceptable excipients may include diluents, disintegrants, binders, solibilizers, stabilizers and lubricants.

In another general aspect, there is provided a stable solid pharmaceutical matrix composition in the form of a tablet comprising sirolimus or pharmaceutically acceptable salts thereof along with one or more sugars in said matrix, wherein the sirolimus or pharmaceutically acceptable salt thereof have a $D_{90}$ particle size less than about 10 μm.

In another general aspect, there is provided a process for the preparation of stable pharmaceutical matrix composition comprising sirolimus or pharmaceutically acceptable salts thereof. The process includes mixing sirolimus or pharmaceutically acceptable salts thereof with one or more sugars, wherein the sirolimus or pharmaceutically acceptable salt thereof have a $D_{90}$ particle size less than about 10 μm.

Embodiments of the pharmaceutical composition may include one or more of the following features. For example, the pharmaceutical composition may further include one or more pharmaceutically acceptable excipients. The pharmaceutically acceptable excipients may include diluents, disintegrants, binders, solibilizers, stabilizers and lubricants.

In another general aspect, there is provided a process for the preparation of stable solid pharmaceutical matrix composition comprising sirolimus or pharmaceutically acceptable salts thereof. The process includes mixing, granulating sirolimus or pharmaceutically acceptable salts thereof with one or more sugars, wherein the sirolimus or pharmaceutically acceptable salt thereof have a $D_{90}$ particle size less than about 10 μm.

In another general aspect, there is provided a stable solid pharmaceutical matrix composition comprising sirolimus or pharmaceutically acceptable salts thereof along with one or more sugars in said matrix, wherein the composition retains at least 80% of the potency of sirolimus or pharmaceutically acceptable salts thereof when stored for three months at 40° and 75% relative humidity for three months, characterized in that sirolimus or pharmaceutically acceptable salt thereof have a $D_{90}$ particle size less than about 10 μm.

Embodiments of the pharmaceutical composition may include one or more of the following features. For example, the pharmaceutical composition may further include one or more pharmaceutically acceptable excipients. The pharmaceutically acceptable excipients may include diluents, disintegrants, binders, solibilizers, stabilizers and lubricants.

In another general aspect, there is provided a stable solid pharmaceutical matrix composition comprising sirolimus or pharmaceutically acceptable salts thereof having $D_{90}$ particle size less than about 10 μm along with one or more sugars in said matrix, wherein the composition exhibits no significant difference in rate and or extent of absorption of sirolimus or pharmaceutically acceptable salts thereof as compared to commercially marketed formulation of sirolimus marketed under the trade name Rapamune® (sirolimus).

In another general aspect, there is provided a stable solid pharmaceutical matrix composition comprising sirolimus or pharmaceutically acceptable salts thereof having $D_{90}$ particle size less than about 10 μm along with one or more sugars in said matrix, wherein the composition exhibits dissolution profile such that at least 80% of sirolimus is released within 30 minutes when carried out in USP Type I, at 120 rpm using 500 ml medium of 0.4% Sodium lauryl sulfate in water.

Embodiments of the pharmaceutical composition may include one or more of the following features. For example, the pharmaceutical composition may further include one or more pharmaceutically acceptable excipients. The pharmaceutically acceptable excipients may include diluents, disintegrants, binders, solibilizers, stabilizers and lubricants.

The details of one or more embodiments of the invention are set forth in the description below. Other features, objects and advantages of the invention will be apparent from the description.

DETAILED DESCRIPTION OF THE INVENTION

The inventors of the invention have discovered that stable solid pharmaceutical compositions of sirolimus or pharmaceutically acceptable salts thereof can be formulated using simple matrix based system wherein the sirolimus and one or more sugars are present in the matrix composition (e.g., in monolithic form) without involving coating procedures as reported in prior art. The compositions of invention are bioequivalent to marketed formulation of sirolimus i.e. Rapamune® (sirolimus), wherein sirolimus and sugars are present in overcoating.

It is possible to use any salts and free base form of sirolimus, including polymorphs, hydrates, solvates or amorphous form.

"$D_{90}$ particle size of 10 μm" as used herein refers to 90% particles having size less than about 10 μm.

In one embodiment, the composition of the present invention contains sirolimus having $D_{90}$ particle size of about 5 μm.

In another embodiment, the composition of the present invention contains sirolimus having $D_{90}$ particle size of about 4 μm.

In another embodiment, the composition of the present invention contains sirolimus having $D_{90}$ particle size of about 2 μm.

The term "matrix", used throughout the specification refers to a continuous solid phase of sirolimus or pharmaceutically acceptable salt thereof and optionally included excipients, for example, matrix is in the form of a monolithic core comprising said continuous solid phase.

The term "sirolimus" used throughout the specification refers to not only sirolimus per se, but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof.

Sirolimus or a pharmaceutically acceptable salt, or the free base, in the composition may be present in an amount of about 0.05 mg to about 20 mg.

Suitable "sugars" may include one or more of lactose, sucrose, derived from beet or cane sources or starch, saccharide, or polysaccharide converted sources, mannitol, sorbitol, xylitol, dextrose, fructose, and the like, it is preferred that the sugar is sucrose. The preferred amount of sugar in the composition ranges from about 20 to 90% w/w.

In an embodiment, the ratio of sirolimus or pharmaceutically acceptable salt thereof to sugar ranges from about 1:45 to about 1:65.

The pharmaceutical composition described herein was found to retain at least 80% of potency of sirolimus or a salt thereof when stored for three months at 40° C. and 40% relative humidity.

The compositions of invention can be developed into dosage form to exhibit immediate release, extended release, sustained release, controlled release, modified release and delayed release or combination thereof. Such compositions can be prepared using rate controlling polymers. Preferably, the composition of the invention is in the form of an extended release composition.

The stable pharmaceutical composition of the present invention exhibits a dissolution profile such that at least 80% of sirolimus is released within 30 minutes when measured in USP Type I apparatus, at 120 rpm using 500 ml medium of 0.4% Sodium lauryl sulfate in water.

The pharmaceutical composition of the invention may include one or more of tablets, capsules, granules, powder, pellets, caplets, minitablets, lozenges, capsule filled with minitablets and/or pellets, multi-layer tablets, granules for suspension, granules or powder filled in a sachet.

The composition of the present invention can be coated to give film-coated tablets.

The composition of the invention may be prepared by mixing pharmaceutically excipients and granulating them with aqueous or alcoholic solution of sirolimus along with sugars optionally with other pharmaceutically acceptable excipients. The granules may be dried and lubricated and converted into a suitable dosage form.

The stable solid pharmaceutical compositions of sirolimus or pharmaceutically acceptable salt thereof may be prepared by processes known to a person having ordinary skill in the art of pharmaceutical technology such as direct compression, wet or dry granulation, slugging, hot melt granulation, hot melt extrusion, fluidized bed granulation, extrusion-spheronization, spray drying and solvent evaporation.

In an embodiment, the stable composition of sirolimus or pharmaceutically acceptable salt thereof is prepared by dry/wet granulating sirolimus or pharmaceutically acceptable salt thereof with one or more sugars and one of more pharmaceutically acceptable excipients, and optionally mixing the granules with other excipients.

The pharmaceutically acceptable excipients may include one or more binders, fillers, lubricants, solubilizers, stabilizers, disintegrants, glidants, and the like.

Suitable "diluents" may include one or more of lactose, microcrystalline cellulose, calcium phosphate, dextrin, dextrose, dextrates, mannitol, sorbitol, sucrose, and the like. In particular, the diluents are lactose and microcrystalline cellulose. The diluent may be present in the extragranular and/or intragranular portions of the composition.

Suitable "disintegrants" may include one or more of crospovidone (polyplasdone), low substituted hydroxypropyl cellulose, carmellose, sodium carboxystarch, calcium carmellose, corn starch, partially-alphatized starch, sodium croscarmellose, sodium starch glycolate, and the like. In particular, the disintegrant is crospovidone. The disintegrant may be present in extragranular and/or intragranular portion of the composition.

Suitable "binders" may include one or more of hydroxypropyl cellulose, hydroxypropylmethyl cellulose, polyvinyl pyrrolidone (povidone K30), polyvinyl alcohol, partial saponificates of these, starch, and the like. In particular, the binder is polyvinyl pyrrolidone.

Suitable "solubilizers" may include one or more of poloxamer, polyethylene glycols, polysorbates, sodium lauryl sulfate, glyceryl monostearate, glyceryl monooleate, lecithin, polyoxythylene alkyl esters, polyoxyethylene castor oil derivatives, polyoxyethylene fatty acid esters, and the like. In particular, the solubilizers are poloxamer and glyceryl monooleate.

Suitable "stabilizers" may include one or more of citric acid, tartaric acid, fumaric acid, maleic acid, vitamin E acetate and the like. In particular, the stabilizer is vitamin E acetate.

Suitable "lubricants/glidants" includes one or more of magnesium stearate, stearic acid, palmitic acid, calcium stearate, zinc stearate, sodium stearyl fumarate, glyceryl behenate, talc, and the like.

The present invention further provides a method of inhibiting organ or tissue transplant rejection in a mammal in need thereof, comprising administering to said mammal a stable solid pharmaceutical matrix composition comprising sirolimus or pharmaceutically acceptable salts thereof along with one or more sugars.

In the context of the present invention, "Bioequivalency" is determined by a 90% Confidence Interval (CI) of between 0.80 and 1.25 for both $C_{max}$ and AUC under USFDA regulatory guidelines, or a 90% CI for AUC of between 0.80 to 1.25 and a 90% CI for Cmax of between 0.70 to 1.43 under the European regulatory guidelines (EMEA).

The term "confidence interval, (CI)" as used herein refers to the plain meaning known to one of ordinary skill in the art. The confidence interval refers to a statistical range with a specified probability that a given parameter lies within the range.

The term "covariance, (CV)" as used herein refers to the plain meaning known to one of ordinary skill in the art. It is a statistical measure of the variance of two random variables that are observed or measured in the same mean time period. This measure is equal to the product of the deviations of corresponding values of the two variables from their respective means.

The bioequivalence studies were carried out between Rapamune® (sirolimus) (reference) and compositions of the invention (test) in fasted and fed state. The study was monitored in terms of $C_{max}$, AUC, $T_{max}$ achieved with the test products and the reference product (Rapamune®) (sirolimus).

At 90% confidence interval; area under the concentration time curve ($AUC_{0-1}$ and/or $AUC_{0-inf}$) and maximum plasma concentration ($C_{max}$) values of composition of the invention lies between 0.70 and 1.70 as compared to that obtained by sirolimus formulation marketed under the trade name Rapamune® (sirolimus).

The results of the relative bioavailability study of sirolimus composition of the invention and sirolimus formulation marketed under the trade name Rapamune® with varying dose and frequency of administration as demonstrated in Table 4 concludes that the formulation explored in the present invention provides equivalent extent of absorption compared to sirolimus formulations marketed under the trade name Rapamune® (sirolimus).

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1

TABLE 1

| Sr. No. | Ingredients | % w/w |
|---|---|---|
| | Intragranular | |
| 1 | Lactose monohydrate | 11.18 |
| 2 | Sucrose | 22.87 |

TABLE 1-continued

| Sr. No. | Ingredients | % w/w |
|---|---|---|
| 3 | Microcrystalline cellulose | 13.21 |
| 4 | Polyplasdone | 3.02 |
| | Granulating vehicle | |
| 5 | Sirolimus | 0.75 |
| 6 | Poloxamer 188 | 0.47 |
| 7 | Glyceryl mono oleate | 0.06 |
| 8 | Vitamin E acetate (liquid) | 0.75 |
| 9 | Citric acid monohydrate | 1.51 |
| 10 | Sucrose | 8.68 |
| 11 | Povidone K30 | 1.70 |
| 12 | Purified water | q.s |
| | Extragranular | |
| 13 | Microcrystalline cellulose | 25.98 |
| 14 | Polyplasdone | 2.64 |
| 15 | Talc | 1.51 |
| | Core Tablet Coating | |
| 16 | Opadry clear | 2.83 |
| 17 | Opadry white | 2.83 |

Procedure:

Lactose monohydrate, sucrose, microcrystalline cellulose and polyplasdone were blended in the fluid bed granulator. The resulting blend was granulated with a granulating vehicle containing sirolimus, poloxamer 188, glyceryl monooleate, vitamin E acetate (liquid), citric acid monohydrate, sucrose, Povidone K30 and water. Then the granules were blended with microcrystalline cellulose, polyplasdone and talc and compressed into tablets. The tablets optionally, film coated with Opadry clear and Opadry white.

Example 2

Dissolution Study

USP, Dissolution apparatus (basket 20 mesh) at 120 rpm using 500 ml medium of 0.4% Sodium lauryl sulfate in water.

TABLE 2

| Time (min) | % dissolution (reference innovator) | Time (min) | % dissolution (test) |
|---|---|---|---|
| 00 | 00.00 | 00.00 | 00.00 |
| 10 | 98.10 | 10 | 93.80 |
| 20 | 101.0 | 20 | 100.0 |
| 30 | 102.7 | 30 | 100.4 |
| 45 | 103.5 | 45 | 100.8 |
| 60 | 103.9 | 60 | 100.9 |
| 120 | 104.8 | 120 | 101.3 |

Example 3

Stability Study

The stability was carried out using 40 cc heavy weight HDPE bottle with 2 g Silica gel at 40° C./75% RH.

TABLE 3

| Related Substance | Limit NMT % | Initial | 1M | 2M | 3M |
|---|---|---|---|---|---|
| Isomer A | 0.50 | 0.05 | 0.02 | 0.14 | 0.04 |
| Total Impurity | 1.00 | 0.88 | 0.98 | 0.79 | 0.96 |

TABLE 3-continued

| Related Substance | Limit NMT % | Initial | 1M | 2M | 3M |
|---|---|---|---|---|---|
| (Excluding Impurity A) | | | | | |
| Unk-RRT (0.29) | 0.20 | 0.16 | 0.18 | 0.14 | 0.18 |
| Unk-RRT (0.40) | 0.20 | 0.04 | 0.04 | 0.01 | 0.05 |
| Unk-RRT (0.50) | 0.20 | 0.09 | 0.06 | 0.06 | 0.05 |
| Unk-RRT (0.57) | 0.20 | 0.14 | 0.13 | 0.12 | 0.10 |
| Unk-RRT (0.70) | 0.20 | 0.12 | 0.14 | 0.02 | 0.08 |
| Unk-RRT (0.82) | 0.20 | 0.03 | 0.11 | 0.17 | 0.19 |
| Assay | | 104.4 | — | — | 102.4 |

Example 4

In Vivo Study

Bioavailability study of the Sirolimus tablet (2 mg) prepared according to example I was carried out on healthy volunteers taking Rapamune® (sirolimus) (2 mg) as the reference, the results of which are represented in Table 4.

TABLE 4

| Parameter | Unit | Reference | Test sample | % T/R ratio |
|---|---|---|---|---|
| Fasting study: | | | | |
| Ln(AUC$^0$-120) | Hr ng/ml | 148.23 | 153.236 | 103.38 |
| Ln(Cmax) | ng/ml | 6.096 | 5.285 | 86.70 |
| Fed study | | | | |
| Ln(AUC$^0$-120) | Hr ng/ml | 97.458 | 97.117 | 99.65 |
| Ln(Cmax) | ng/ml | 6.617 | 6.157 | 93.04 |

While the invention has been described in terms of its specific embodiments, certain modifications and equivalents will be apparent to those skilled in the art and are intended to be included within the scope of the invention.

We claim:

1. A stable solid pharmaceutical matrix composition comprising sirolimus or a pharmaceutically acceptable salt thereof along with one or more sugars selected from sucrose, dextrose, fructose, mannitol, xylitol and sorbitol, wherein the sugar is present in the matrix in an amount of 31.55% by weight of total composition and wherein the sirolimus or a pharmaceutically acceptable salt thereof have a $D_{90}$ particle size of less than about 10 μm.

2. The stable pharmaceutical composition as claimed in claim 1, wherein the matrix is in monolithic form.

3. The stable pharmaceutical composition as claimed in claim 1, wherein the sirolimus or a pharmaceutically acceptable salt thereof have a $D_{90}$ particle size of about 4 μm.

4. The stable pharmaceutical composition as claimed in claim 1, wherein the sirolimus or pharmaceutically acceptable salt thereof is present in an amount from about 0.05 mg to about 20 mg.

5. The stable pharmaceutical composition as claimed in claim 1, further comprising one or more diluents, disintegrants, binders, solubilizers, stabilizers and lubricants.

6. The stable pharmaceutical composition as claimed in claim 1, wherein the composition is in the form of a tablet, a capsule, granules, powder, pellets, a caplet, minitablets, lozenges, capsule filled with minitablets and/or pellets, multilayer tablet, granules for suspension, granules and powder filled in sachet.

7. The stable pharmaceutical composition as claimed in claim 1, wherein the composition exhibits a dissolution profile such that at least 80% of the sirolimus is released within 30 minutes when measured in USP Type I, at 120 rpm using 500 ml medium of 0.4% sodium lauryl sulfate in water.

8. The stable pharmaceutical composition as claimed in claim 1, wherein the composition exhibits no significant difference in rate and/or extent of absorption of sirolimus or pharmaceutically acceptable salts thereof as compared to commercially marketed formulation of sirolimus marketed under trade name Rapamune®.

9. A stable solid pharmaceutical matrix composition comprising a core of sirolimus or pharmaceutically acceptable salts thereof and one or more sugars, wherein the composition retains at least 80% of the potency of the sirolimus when stored for three months at 40° C. and 75% relative humidity.

10. The stable pharmaceutical composition of sirolimus as claimed in claim 1 comprising:
    (a) about 0.75% w/w of sirolimus;
    (b) 31.55% w/w of sucrose;
    (c) about 11.18% w/w of lactose monohydrate;
    (d) about 13.21% w/w of microcrystalline cellulose;
    (e) about 5.66% w/w of crospovidone;
    (f) about 0.47% w/w of poloxomer 188;
    (g) about 0.06% w/w of glyceryl mono oleate;
    (h) about 0.75% w/w of vitamin E acetate;
    (i) about 1.51% w/w of citric acid monohydrate;
    (j) about 1.70% w/w of povidone K30; and
    (k) about 1.51% w/w of talc.

11. The stable pharmaceutical composition as claimed in claim 10, wherein the crospovidone and/or microcrystalline cellulose are present both in intragranular and extragranular portions.

12. A process for the preparation of stable pharmaceutical solid matrix composition according to claim 1 comprising sirolimus or pharmaceutically acceptable salts thereof, the process comprising mixing or granulating the sirolimus or pharmaceutically acceptable salts thereof with one or more sugars.

13. The process of preparing the stable pharmaceutical composition as claimed in claim 12, wherein the process comprising the steps of: (a) mixing lactose monohydrate, sucrose, microcrystalline cellulose and crospovidone; (b) preparing a granulating vehicle of sirolimus using poloxamer 188, sucrose, and water; (c) granulating the mixture of step (a) using the granulating vehicle prepared in step (b); (d) blending the resulting granules with microcrystalline cellulose, crospovidone and talc; (e) converting the granules prepared in step (d) into a suitable dosage form; and (f) optionally, film coating the dosage form.

14. The process of preparing the stable pharmaceutical composition as claimed in claim 13, wherein the granulating vehicle of sirolimus further comprises glyceryl mono oleate, vitamin E acetate, citric acid monohydrate and povidone K30.

15. A method of inhibiting organ or tissue transplant rejection in a mammal in need thereof, the method comprising administering to said mammal a stable solid pharmaceutical matrix composition according to claim 1 comprising sirolimus or pharmaceutically acceptable salts thereof along with one or more sugars.

* * * * *